United States Patent
Wu et al.

(10) Patent No.: US 6,187,984 B1
(45) Date of Patent: Feb. 13, 2001

(54) DEHYDROGENATION OF N-BUTANE TO BUTENES

(75) Inventors: An-hsiang Wu, Bartlesville; Charles A. Drake, Nowata, both of OK (US)

(73) Assignee: Phillips Petroleum Company, Bartlesville, OK (US)

(*) Notice: Under 35 U.S.C. 154(b), the term of this patent shall be extended for 0 days.

(21) Appl. No.: 09/599,369

(22) Filed: Jun. 22, 2000

Related U.S. Application Data

(62) Division of application No. 09/222,470, filed on Dec. 29, 1998, now Pat. No. 6,133,192.

(51) Int. Cl.$^7$ .................................................. C07C 5/333
(52) U.S. Cl. ..................... 585/660; 585/654; 585/656; 585/657; 585/658
(58) Field of Search ................................. 585/654, 660, 585/656, 657, 658

(56) References Cited

U.S. PATENT DOCUMENTS

| | | |
|---|---|---|
| 3,531,543 | 9/1970 | Clippinger et al. . |
| 3,745,112 * | 7/1973 | Rausch ................................. 208/139 |
| 3,779,947 * | 12/1973 | Mitsche et al. ..................... 502/334 |
| 3,864,284 | 2/1975 | Clippinger et al. . |
| 3,880,776 | 4/1975 | Box et al. . |
| 3,909,451 | 9/1975 | Wilhelm . |
| 3,929,683 * | 12/1975 | Antos .................................... 502/334 |
| 3,939,220 * | 2/1976 | Rausch ................................. 208/138 |
| 4,014,783 * | 3/1977 | Rausch ................................. 208/143 |
| 4,048,245 | 9/1977 | Pollitzer et al. . |
| 4,221,738 * | 9/1980 | Imai ..................................... 502/334 |
| 4,982,047 | 1/1991 | Barri et al. ........................... 585/660 |
| 5,344,805 * | 9/1994 | Khare et al. ......................... 502/329 |
| 5,358,920 | 10/1994 | Ma et al. ............................. 502/330 |
| 5,877,369 * | 3/1999 | Wu et al. ............................. 585/419 |
| 5,898,011 * | 4/1999 | Wu et al. .............................. 502/60 |

* cited by examiner

*Primary Examiner*—Elizabeth D. Wood
(74) *Attorney, Agent, or Firm*—Richmond, Hitchcock, Fish & Dollar

(57) ABSTRACT

A catalyst composition suitable for the conversion of n-butane to butenes. The same catalyst composition that with chlorination is further suitable, when used in the conversion of n-butane, for the production of an increased amount of BTX (benzene-toluene-xylene) and greater selectivity to the production of isobutylenes than attained with the unchlorinated catalyst. A process for the preparation of catalyst compositions suitable for the conversion of n-butane. Use of the catalyst compositions in processes for the conversion of n-butane.

10 Claims, No Drawings

US 6,187,984 B1

DEHYDROGENATION OF N-BUTANE TO BUTENES

This application is a Division of application Ser. No. 09/222,470, filed Dec. 29, 1998 now U.S. Pat. No. 6,133,192.

FIELD OF THE INVENTION

The invention relates to a catalyst suitable for the dehydrogenation of n-butane to butenes that with chlorination is further suitable, when used in the conversion of n-butane, for the production of an increased amount of BTX (benzene-toluene-xylene) and greater selectivity to the production of isobutylenes than attained with the unchlorinated catalyst; a process for the preparation of catalyst suitable for the conversion of n-butane and the use of the catalyst in processes for the conversion of n-butane.

BACKGROUND OF THE INVENTION

It is known that n-butane can be converted to other hydrocarbons in the presence of variety of catalyst supports impregnated with a variety of metals. A catalyst composition prepared according to a process of this invention has been found to be suitable for use in the dehydrogenation of n-butane to butenes. It has also been found that upon chlorination of this catalyst its suitability for use in the production of BTX from n-butane is improved.

SUMMARY OF THE INVENTION

It is an object of this invention to at least partially dehydrogenate n-butane to butenes.

Another object of this invention is to provide an improved alumina-based catalyst that can be utilized in the dehydrogenation of n-butane to butenes.

A further object of this invention is to provide a method for making an alumina-based catalyst that can be utilized in the dehydrogenation of n-butane to butenes.

It is another object of this invention to provide a chlorinated alumina-based catalyst.

Another object of the invention is to utilize a chlorinated alumina-based catalyst in the production of BTX from n-butane.

Still another object of the invention is to provide a method for preparing a chlorinated alumina-based catalyst that can be utilized in the production of BTX from n-butane.

The invention is an alumina-based catalyst that is prepared by impregnation with tin, steam treatment, impregnation with platinum and calcination in air to provide a catalyst composition and a process in which a feedstock containing n-butane is passed in contact with this catalyst composition under conditions to produce butenes. The invention also includes a catalyst composition prepared by the chlorination of the catalyst produced as set out above and a process in which a feedstock containing n-butane is passed in contact with this catalyst composition under conditions to produce BTX.

Other objects and advantages of the invention will become apparent from the detailed description and the appended claims.

DETAILED DESCRIPTION OF THE INVENTION

The alumina used in making the inventive compositions can be any alumina which when contacted with a feedstock containing n-butane under suitable operating conditions is not detrimental to the conversion of n-butane to butenes. The alumina can be alpha-alumina, beta-alumina, gamma-alumina, eta-alumina, delta-alumina, or combinations of any two or more thereof. The presently preferred alumina is gamma-alumina having a surface area in the range of about 40 $m^2/g$ to about 300 $m^2/g$, a total pore volume in the range of about 0.1 ml/g to about 1 ml/g. These aluminas are commercially available as extrudate pellets.

According to the present invention any tin-containing compound which when combined with alumina is effective in producing butenes from the conversion of n-butane can be employed. Examples of preferred compounds are organic tin compounds that can be dissolved in organic solvents, these include, but are not limited to, tributyl tin acetate, trimethyltin, tetra-n-propyltin, tributyl tin hydride, trimethyl tin hydroxide, tri-n-propyltin hydroxide, tri-n-propyltin acetate, and mixtures of two or more thereof. Tributyl tin acetate is most preferred.

The amount of tin incorporated or impregnated into the alumina should provide a concentration effective to assure predetermined butene conversion yields employing the catalyst composition in the selective dehydrogenation of feedstock that contains n-butane. Generally, the weight percent of tin present in the impregnated alumina is in a range of about 0.001 to about 10 weight percent of the impregnated alumina composition. The preferred concentration of tin in the impregnated zeolite is in the range of about 0.01 to about 5 weight percent and, more preferably, from about 0.1 to about 2 weight percent of the impregnated zeolite composition.

It is essential to this invention that the alumina impregnated with tin be treated in the presence of steam at an elevated temperature. In the preferred embodiment of the invention the alumina impregnated with tin is a tin-aluminate.

Generally, this steam treatment can be conducted at a pressure in a range from below atmospheric pressure to about 1000 pounds per square inch absolute (psia). More typically, however, the pressure range is from about atmospheric to about 100 psia. The temperature of this steam treatment is generally in the range of about 400° C. to about 1000° C. Preferably, this temperature range is from about 500° C. to about 850° C. and, most preferably, the temperature of this heat treatment is in a range of about 550° C. to about 750° C.

The steam treated tin-aluminate is then impregnated with a platinum compound. Generally, any platinum-containing compound can be employed in the process of this invention. Examples of suitable platinum compounds include, but are not limited to, chloroplatinic acid, platinic chloride, platinum bromide, platinum iodide, tetramine platinum chloride, tetramine platinum nitrate, tetramine platinum hydroxide, tetrachlorodiamine platinum and combinations of any two or more thereof. Chloroplatinic acid is preferred.

The impregnating solution is an aqueous solution to which can be added a small amount of acid to aid in stabilizing the impregnating solution. Presently, when chloroplatinic acid, the preferred platinum compound, is used, hydrochloric acid (HCl) is added to the impregnating solution in an amount up to about 2 weight percent of the total aqueous impregnating solution.

The amount of platinum incorporated or impregnated into the tin-containing composition should provide a concentration effective to assure predetermined butene conversion yields employing the catalyst composition in the selective dehydrogenation of feedstock that contains n-butane. Generally, the weight percent of platinum present in the impregnated alumina is in a range of about 0.001 to about 10 weight percent of the impregnated zeolite composition. The preferred concentration of platinum in the impregnated zeolite is in the range of about 0.01 to about 5 weight percent and, more preferably, from about 0.1 to about 2 weight percent of the impregnated zeolite composition.

The platinum-impregnated tin-containing catalyst composition is treated at an elevated temperature in the presence of an oxygen containing atmosphere, preferably air. Generally, this calcination can be conducted at a pressure in a range from below atmospheric pressure to about 1000 pounds per square inch absolute (psia). More typically, however, the pressure range is from about atmospheric to about 100 psia. The temperature of this heat treatment is generally in the range of about 400° C. to about 800° C. Preferably, this temperature range is from about 450° C. to about 700° C. and, most preferably, the temperature of this heat treatment is in a range of about 500° C. to about 600° C.

The chlorination of the calcined tin-aluminate containing platinum can be carried out by heating with a gas containing hydrogen an at least one chlorine-containing compound which can be HCl, a chloroalkane or mixture of these chlorination agents. Suitable chloroalkanes, which generally contain 1–4 carbon atoms per molecule and 1–6 chlorine atoms per molecule, can be, but are not limited to, chloromethane, dichloromethane, trichloromethane, carbon tetrachloride, chloroethane, 1,1-dichloroethane, 1,2-dichloroethane, trichloroethanes, tetrachloroethanes, hexachloroethanes, 1-chloropropane, 2-chloropropane, 1,2-dichloropropane, 1,3-dichloropropane, 2,2-dichloropropane, trichloropropanes, tetrachloropropanes, chlorobutanes, dichlorobutanes, trichlorobutanes, tetrachlorobutanes, and the like, and mixtures thereof. HCl is the preferred chlorination agent for this invention.

The molar ratio of hydrogen to the chlorinating agent is generally about 0.01:1 to about 100:1, preferably from about 0.05:1 to about 50:1, and more preferably from about 0.2:1 to about 20:1. It is also within the scope of this invention to have an inert diluent such as nitrogen, helium, neon or argon present in the chlorination gas mixture.

The chlorination is carried out at a temperature in the range of about 50° C. to about 700° C., preferably from about 150° C. to about 600° C., more preferably from about 300° C. to about 500° C. After the material is chlorinated it is cooled to room temperature, preferably in an inert atmosphere.

The processes of this invention applies most specifically to the conversion of n-butane to butenes and BTX. The feedstock can be any feedstock that contains n-butane. The higher the content of n-butane the more preferred is a feedstock for this invention. Among the feedstocks for which this invention is useful are those having a content of cracked hydrocarbon feedstocks from the catalytic cracking e.g. fluidized catalytic cracking and hydrocracking) of gas oils and the thermal cracking of light hydrocarbons, naphthas, gas oils, reformates and straight-run gasoline. The cracked gasoline feedstock generally comprises hydrocarbons containing 2–16 carbon atoms per molecule chosen from among paraffins (alkanes) and/or olefins (alkenes) and/or naphthenes (cycloalkanes). A more preferred feedstock for the process of this invention is a cracked gasoline derived from the fluidized catalytic cracking of gas oil, suitable for use as at least a gasoline blend stock generally having a boiling range of from about 80° F. to about 430° F. The boiling range of the cracked hydrocarbon feedstock is determined by the standard ASTM method for measuring the initial boiling point and the end-point temperatures. Generally the content of paraffins exceeds the combined content of olefins, naphthenes, and aromatics (if present).

Feedstock containing n-butane and the catalyst compositions can be contacted within a reaction zone in any suitable manner. The contacting can be operated with a catalyst bed in a reactor vessel as a batch process or, preferably, as a continuous process. In either a batch or a continuous process a solid catalyst bed can be employed. Both the batch and continuous modes of operation have known advantages and disadvantages so that one skilled in the art can select the mode most suitable for a particular feedstock to be contacted with the inventive catalyst arrangement.

Contacting the feedstock containing n-butane and the catalyst composition is carried out in a reaction zone containing the catalyst compositions while employing reaction conditions that promote the conversion of n-butane with the formation of butenes and, with the chlorinated catalyst, the formation of BTX. The reaction temperature employed in the contacting is in the range of from about 300° C. to about 800° C., preferably, from about 400° C. to about 700° C. and, more preferably, from 500° C. to about 600° C. The pressure employed in the contacting can range from subatmospheric up to about 500 psia and, preferably, from about atmospheric to about 400 psia.

The flow rate at which the feedstock is charged to the conversion reaction zone for contact with the catalyst composition is selected to provide a weight hourly space velocity (WHSV) in a range having an upward limit of about 1000 hour$^{-1}$. The term "weight hourly space velocity", as used herein, shall mean the numerical ratio of the rate at which a cracked hydrocarbon feedstock is charged to the conversion reaction zone in pounds per hour divided by the pounds of catalyst contained in the conversion reaction zone to which the hydrocarbon is charged. The preferred WHSV of the feed to the conversion reaction zone, or contacting zone, can be in the range of from about 0.25 hour$^{-1}$ to about 250 hour$^{-1}$ and, more preferably, from about 0.5 hour$^{-1}$ to about 100 hour$^{-1}$.

The following examples are presented to further illustrate this invention and are not to be construed as unduly limiting its scope.

EXAMPLE I

This example illustrates the preparation of catalysts which were subsequently tested as catalysts in the conversion of n-butane to butenes.

Catalyst A: Co-Impregnation of Alumina Support with Platinum and Tin

A 37 percent solution of HCl in water was added to a mixture of chloroplatinic acid and hydrated tin chloride ($SnCl_2.2H_2O$) to form a solution having 1 wt percent of chloroplatinic acid, 0.65 wt percent of tin chloride, 8.35 wt percent HCl and 90 wt percent water.

A quantity of 15.27 g of CS-331 alumina, obtained from UCI (United Catalysts, Inc., Louisville, Ky.), was admixed with 9.29 g of the solution produced above. The admixture was treated at 538° C. with air flow for 6 hours to provide 14.46 g of platinum-incorporated tin aluminate catalyst having a content of 0.244 wt percent platinum and 0.220 wt percent tin.

Catalyst B: Co-Impregnation of Alumina Support with Platinum and Tin

A 37 percent solution of HCl in water was added to a mixture of chloroplatinic acid and hydrated tin chloride ($SnCl_2 \cdot 2H_2O$) to form a solution having 1 wt percent of chloroplatinic acid, 0.65 wt percent of tin chloride, 8.35 wt percent HCl and 90 wt percent water.

A quantity of 9.37 g of CS-331 alumina, obtained from UCI (United Catalysts, Inc., Louisville, Ky.), was admixed with 6.38 g of the solution produced above. The admixture was treated at 538° C. with air flow for 6 hours to provide 8.80 g of platinum-incorporated tin aluminate catalyst having, a content of 0.276 wt percent platinum and 0.191 wt percent tin.

Catalyst C. Co-Impregnation of Alumina Support with Platinum and Tin

A 37 percent solution of HCl in water was added to a mixture of chloroplatinic acid and hydrated tin chloride ($SnCl_2 \cdot 2H_2O$) to form a solution having 1 wt percent of chloroplatinic acid, 0.65 wt percent of tin chloride, 8.35 wt percent HCl and 90 wt percent water.

A quantity of 10.00 g of CS-331 alumina, obtained from UCI (United Catalysts, Inc., Louisville, Ky.), was admixed with 7.82 g of the solution produced above. The admixture was treated at 538° C. with air flow for 6 hours to provide 9.54 g of platinum-incorporated tin aluminate catalyst having a content of 0.311 wt percent platinum and 0.280 wt percent tin.

Catalyst D: Impregnation of Alumina Support with Platinum

A quantity of 10.00 g of CS-331 alumina, obtained from UCI (United Catalysts, Inc., Louisville, Ky.), was admixed with 6.57 g of a solution containing 1 percent chloroplatinic acid, 1 percent HCl and 98 percent $H_2O$. The admixture was treated at 538° C. with air flow for 6 hours to provide 9.47 g of platinum-incorporated aluminate catalyst having a content of 0.264 wt percent platinum.

Catalyst E: Sequential Impregnation of Alumina Support with Tin and Platinum A quantity of 10.00 g of CS-331 alumina, obtained from UCI (United Catalysts, Inc., Louisville, Ky.), was admixed with 5.20 g of a solution containing 1 wt percent tributyltin ($Bu_3SnOAc$) in $C_{4-6}$ solution. The mixture was treated with steam at 650° C. for 6 hours to provide 9.46 g of tin aluminate. A quantity of 10 g of the tin aluminate was admixed with 6.93 g of a solution containing 1 percent chloroplatinic acid, 1 percent HCl and 98 percent $H_2O$. The admixture was treated at 538° C. with air flow for 6 hours to provide 9.39 g of platinum-incorporated tin-aluminate catalyst having a content of 0.280 wt percent platinum and 0.187 wt percent tin.

Catalyst F. Sequential Impregnation of Alumina Support with Tin and Platinum A quantity of 10.00 g of CS-331 alumina, obtained from UCI (United Catalysts, Inc., Louisville, Ky.), was admixed with 5.37 g of a solution containing 1.5 wt percent tributyltin ($Bu_3SnOAc$) in $C_{4-6}$ solution. The mixture was treated with steam at 650° C. for 6 hours to provide 9.46 g of tin aluminate. The tin aluminate was admixed with 6.81 g of a solution containing 1 percent chloroplatinic acid, 1 percent HCl and 98 percent $H_2O$. The admixture was treated at 538° C. with air flow for 6 hours to provide 9.32 g of platinum-incorporated tin-aluminate catalyst having a content of 0.278 wt percent platinum and 0.290 wt percent tin.

Catalyst G: Sequential Impregnation of Alumina Support with Tin and Platinum A quantity of 10.00 g of CS-331 alumina, obtained from UCI (United Catalysts, Inc., Louisville, Ky.), was admixed with 4.91 g of a solution containing 3.0 wt percent tributyltin ($Bu_3SnOAc$) in $C_{4-6}$ solution. The mixture was treated with steam at 650° C. for 6 hours to provide 9.48 g of tin aluminate. The tin aluminate was admixed with 7.20 g of a solution containing 1 percent chloroplatinic acid, 1 percent HCl and 98 percent $H_2O$. The admixture was treated at 538° C. with air flow for 6 hours to provide 9.44 g of platinum-incorporated tin-aluminate catalyst having a content of 0.290 wt percent platinum and 0.528 wt percent tin.

Catalyst H: Sequential Impregnation of Alumina Support with Tin and Platinum A quantity of 10.00 g of CS-331 alumina, obtained from UCI (United Catalysts, Inc., Louisville, Ky.), was admixed with 5.20 g of a solution containing 1.5 wt percent tributyltin ($Bu_3SnOAc$) in $C_{4-6}$ solution. The mixture was treated with air at 538° C. for 6 hours to provide 9.39 g of tin aluminate. The tin aluminate was admixed with 6.88 g of a solution containing 1 percent chloroplatinic acid, 1 percent HCl and 98 percent $H_2O$. The admixture was treated at 538° C. with air flow for 6 hours to provide 9.42 g of platinum-incorporated tin-aluminate catalyst having a content of 0.278 wt percent platinum and 0.282 wt percent tin.

EXAMPLE II

This example illustrates the use of the Zeolite materials described in Example I as catalysts in the conversion of n-butane to butenes.

For each of the test runs, a sample of about 2.8 g of the catalyst materials described in Example I was placed into a stainless steel tube reactor (length: about 18 inches; inner diameter: about 0.5 inch). An n-butane feedstock was passed through the reactor at a flow rate of about 5 WHSV, at a temperature of about 550° C. and at atmospheric pressure (about 0 psig). Hydrogen, at a rate of 1.2 L/hr and a mol ratio of hydrogen to hydrocarbon of about 2.2, was used a carrier gas for all catalysts. The formed reaction product exited the reactor tube and passed through several ice-cooled traps. The liquid portion remained in these traps and was weighed. The volume of the gaseous portion which exited the traps was measured in a "wet test meter". Liquid and gaseous product samples (collected at hourly intervals) were analyzed by means of a gas chromatograph. Results of the test runs for Catalysts A through H are summarized in Table I. All test data were obtained up to about 6 hours on stream.

In Table I, immediately following, is listed the weight percent of platinum and tin in the catalysts tested. The tin and platinum are incorporated into the catalyst either by co-impregnation, impregnation or sequentially and the thermal decomposition of the catalyst is accomplished using air calcination or a combination of steam treating and calcination with air. The table also shows the percent conversion of n-butane into butenes and the selectivity toward butenes and isobutylene.

TABLE I n-Butane Conversion Catalyzed with Pt/SnAl₂Ox

| Catalyst | Pt Wt % | Sn Wt % | Sn & Pt Incorp. | Thermal Decomp. | % Conv. n - C₄ | Wt. % C₄₌ | Select. C₄⁻ | Select. I - C₄⁻ |
|---|---|---|---|---|---|---|---|---|
| A | 0.244 | 0.220 | Co-imp | AC | 34.507 | 19.565 | 0.567 | 0.354 |
| B | 0.276 | 0.191 | Co-imp | AC | 65.915 | 12.595 | 0.191 | 0.335 |
| C | 0.311 | 0.280 | Co-imp | AC | 13.298 | 5.707 | 0.429 | 0.286 |
| D | 0.264 | 0.000 | Imp | AC | 15.620 | 10.613 | 0.679 | 0.284 |
| E | 0.280 | 0.187 | Sequent. | STM-AC | 36.269 | 29.293 | 0.808 | 0.182 |
| F | 0.278 | 0.290 | Sequent. | STM-AC | 31.770 | 25.760 | 0.811 | 0.165 |
| G | 0.290 | 0.528 | Sequent. | STM-AC | 22.946 | 19.152 | 0.835 | 0.124 |
| H | 0.278 | 0.282 | Sequent. | AC-AC | 26.734 | 21.122 | 0.790 | 0.201 |

A comparison of the products of the n-butane conversions shows that Catalysts E–G impregnated sequentially and treated sequentially with steam and air provide both better activity and better selectivity toward butene production than either the co-impregnated Catalysts A–D or the sequentially impregnated catalyst treated only by air calcination (Catalysts A–D and H). A direct comparison between the sequential steam/air treatment and a sequential air/air treatment can be made noting the conversion of n-butane, butenes produced and the selectivity to butenes and isobutylene using Catalyst F as compared to using Catalyst H. In the comparison the much higher conversion of n-butane to $C_4$ is an economic compensation for the slightly lower selectivity to isobutylene.

EXAMPLE III

This example illustrates the preparation of catalysts which were subsequently tested as catalysts in the conversion of n-butane to butenes.

Catalyst I: Impregnation of Alumina Support with Platinum

A quantity of 10 g of CS-331 alumina, obtained from UCI (United Catalysts, Inc., Louisville, Ky.), was admixed with 6.57 g of a solution containing 1 percent chloroplatinic acid, 1 percent HCl and 98 percent $H_2O$. The admixture was treated at 538° C. with air flow for 6 hours to provide 9.47 g of platinum-incorporated alumina catalyst having a content of 0.264 wt percent platinum.

Catalyst J: Chlorination of Platinum Impregnated Alumina Support

A quantity of 7.01 g of Catalyst I was treated with a flow of 100 mL per minute of hydrogen and 20 mL per minute of hydrochloric acid (HCl) at a temperature of 400° C. for 1 hour to produce 6.99 g of chlorinated platinum impregnated alumina.

Catalyst K: Impregnation of Alumina Support with Tin and Platinum

A quantity of 10 g of CS-331 alumina, obtained from UCI (United Catalysts, Inc., Louisville, Ky.), was admixed with 5.20 g of a solution containing 1.0 wt percent tributyltin ($Bu_3SnOAc$) in $C_{4-6}$ solution. The mixture was treated with air at 538° C. for 6 hours to provide 9.46 g of tin aluminate. The tin aluminate was admixed was admixed with 6.93 g of a solution containing 1 percent chloroplatinic acid, 1 percent HCl and 98 percent $H_2O$. The admixture was treated at 538° C. with air flow for 6 hours to provide 9.39 g of platinum-incorporated tin-aluminate catalyst having a content of 0.280 wt percent platinum and 0.187 wt percent tin with an atomic ration of Sn/Pt=1.097.

Catalyst L: Chlorination of Platinum Impregnated Tin-aluminate

A quantity of 6.58 g of Catalyst K was treated with a flow of 100 mL per minute of hydrogen and 20 mL per minute of hydrochloric acid (HCl) at a temperature of 400° C. for 1 hour to produce 6.62 g of chlorinated platinum impregnated tin-aluminate.

Catalyst M: Impregnation of Alumina Support with Tin and Platinum

A quantity of 10 g of CS-331 alumina, obtained from UCI (United Catalysts, Inc., Louisville, Ky.), was admixed with 5.37 g of a solution containing 1.5 wt percent tributyltin ($Bu_3SnOAc$) in $C_{4-6}$ solution. After the temperature was raised to the treatment temperature over a period of 2 hours the mixture was treated with steam at 650° C. for 6 hours to provide 9.46 g of tin aluminate. The tin aluminate was admixed with 6.81 g of a solution containing 1 percent chloroplatinic acid, 1 percent HCl and 98 percent $H_2O$. The admixture was treated at 538° C. with air flow for 6 hours to provide 9.32 g of platinum-incorporated tin-aluminate catalyst having a content of 0.278 wt percent platinum and 0.290 wt percent tin with an atomic ratio of Sn/Pt=1.713.

Catalyst N: Chlorination of Platinum Impregnated Tin-aluminate

A quantity of 6.60 g of Catalyst M was treated with a flow of 100 mL per minute of hydrogen and 20 mL per minute of hydrochloric acid (HCl) at a temperature of 400° C. for 1 hour to produce 6.65 g of chlorinated platinum impregnated tin-aluminate.

Catalyst P: Impregnation of Alumina Support with Tin and Platinum

A quantity of 10 g of CS-331 alumina, obtained from UCI (United Catalysts, Inc., Louisville, Ky.), was admixed with 4.91 g of a solution containing 3.0 wt percent tributyltin ($Bu_3SnOAc$) in $C_{4-6}$ solution. The mixture was treated with air at 538° C. for 6 hours to provide 9.48 g of tin aluminate. The tin aluminate was admixed with 6.48 g of a solution containing 1 percent chloroplatinic acid, 1 percent HCl and 98 percent $H_2O$. The admixture was treated at 538° C. with air flow for 6 hours to provide 9.44 g of platinum-incorporated tin-aluminate catalyst having a content of 0.290 wt percent platinum and 0.528 wt percent tin with an atomic ration of Sn/Pt=2.991.

Catalyst Q: Chlorination of Platinum Impregnated Tin-aluminate

A quantity of 6.55 g of Catalyst P was treated with a flow of 100 mL per minute of hydrogen and 20 mL per minute of hydrochloric acid (HCl) at a temperature of 400° C. for 1 hour to produce 6.57 g of chlorinated platinum impregnated tin-aluminate.

EXAMPLE IV

This example illustrates the use of the catalyst materials described in Example III as catalysts in the conversion of n-butane to benzene-toluene-xylene (BTX) and $C_4$, particularly isobutylenes.

For each of the test runs, a sample of from about 2.5 to 2.9 g of the catalyst materials described in Example III was placed into a stainless steel tube reactor (length: about 18 inches; inner diameter: about 0.5 inch). The temperature was raised 10° C./min to the reaction temperature of 500° C. while the catalyst was pretreated with a flow of 300 mL/minute of hydrogen. An n-butane feedstock was passed through the reactor at a flow rate of about 5 WHSV, at a temperature of about 550° C. and at atmospheric pressure (about 0 psig). Hydrogen, at a rate of 1.2 L/hr and a mol ratio of hydrogen to hydrocarbon of about 2.2, was used a carrier gas for all catalysts. The formed reaction product exited the reactor tube and passed through several ice-cooled traps. The liquid portion remained in these traps and was weighed. The volume of the gaseous portion which exited the traps was measured in a "wet test meter". Liquid and gaseous product samples (collected at hourly intervals) were analyzed by means of a gas chromatograph. Results of the test runs for Catalysts A through H are summarized in Table I. All test data were obtained up to about 6 hours on stream.

In Table II, immediately following, illustrating the conversion of n-butane using a chlorinated platinum impregnated tin-aluminate is listed the weight percent of platinum and tin in the catalysts tested. The table also shows the percent conversion of n-butane into BTX (benzene-toluene-xylene) and butenes and the selectivity toward isobutylene.

TABLE II n-Butane Conversion Catalyzed with [Cl]Pt/SnAl$_2$Ox

| Catalyst | Wt % Comp. Pt | Sn | At. Ratio Sn/Pt | n – $C_4$ Wt % Conv. | Wt % Formed BTX | $C_4$⁻s | Select. i – $C_4$⁻ |
|---|---|---|---|---|---|---|---|
| I | 0.264 | 0.000 | 0.000 | 15.620 | 1.322 | 10.613 | 0.284 |
| J | 0.264 | 0.000 | 0.000 | 50.575 | 35.127 | 7.970 | 0.351 |
| K | 0.280 | 0.187 | 1.097 | 34.205 | 2.282 | 28.203 | 0.173 |
| L | 0.280 | 0.187 | 1.097 | 53.613 | 21.037 | 24.516 | 0.325 |
| M | 0.278 | 0.290 | 1.713 | 31.770 | 2.645 | 25.762 | 0.165 |
| N | 0.278 | 0.290 | 1.713 | 71.067 | 46.871 | 16.011 | 0.313 |
| P | 0.290 | 0.528 | 2.991 | 20.994 | 0.000 | 17.404 | 0.118 |
| Q | 0.290 | 0.528 | 2.991 | 75.058 | 53.367 | 13.375 | 0.315 |

The data above illustrate the superiority of the chlorinated catalysts as compared to the same catalyst without chlorination in the production of BTX and in their selectivity toward isobutylenes.

Reasonable variations, modifications and adaptations can be made within the scope of the disclosure and the appended claims without departing from the scope of this invention.

What is claimed is:

1. A method for the dehydrogenation of n-butane to butenes comprising contacting a feedstock containing n-butane under reaction conditions suitable for the conversion of n-butane to butenes in the presence of a catalyst composition prepared according to the method comprising:
   (A) impregnating alumina with a tin compound to provide alumina impregnated with tin;
   (B) subsequently steam treating the alumina impregnated with tin at an elevated temperature to provide a steam treated tin-aluminate;
   (C) impregnating the steam treated tin-aluminate with a platinum compound to provide a platinum containing tin-aluminate and
   (D) treating the platinum impregnated tin-aluminate in air at a calcining temperature to provide a calcined platinum containing tin-aluminate.

2. A method for the dehydrogenation of n-butane to butenes, according to claim 1 wherein the alumina is gamma alumina.

3. A method for the dehydrogenation of n-butane to butenes according to claim 2 wherein the tin compound is chosen from the group consisting of tributyl tin acetate, trimethyltin, tetra-n-propyltin, tributyl tin hydride, trimethyl tin hydroxide, tri-n-propyltin hydroxide, tri-n-propyltin acetate, and mixtures of two or more thereof.

4. A method for the dehydrogenation of n-butane to butenes according to claim 3 wherein the weight percent of tin present in the impregnated alumina is in a range of about 0.001 to about 10 weight percent of the impregnated alumina composition.

5. A method for the dehydrogenation of n-butane to butenes according to claim 4 wherein the tin compound is tributyl tin acetate.

6. A method for the dehydrogenation of n-butane to butenes according to claim 4 wherein the steam treatment is in a temperature range of about 400° C. to about 1000° C.

7. A method for the dehydrogenation of n-butane to butenes according to claim 5 wherein the steam treatment is in a temperature range of about 400° C. to about 1000° C.

8. A method for the dehydrogenation of n-butane to butenes according to claim 6 wherein the platinum compound is chosen from the group consisting of chloroplatinic acid, platinic chloride, platinum bromide, platinum iodide, tetramine platinum chloride, tetramine platinum nitrate, tetramine platinum hydroxide, tetrachlorodiamine platinum and combinations of any two or more thereof.

9. A method for the dehydrogenation of n-butane to butenes according to claim 7 wherein the platinum compound is chosen from the group consisting of chloroplatinic acid, platinic chloride, platinum bromide, platinum iodide, tetramine platinum chloride, tetramine platinum nitrate, tetramine platinum hydroxide, tetrachlorodiamine platinum and combinations of any two or more thereof.

10. A method for the dehydrogenation of n-butane to butenes according to claim 1 wherein the calcining treatment is in a temperature range of about 400° C. to about 800° C.

\* \* \* \* \*